(12) United States Patent
Streicher et al.

(10) Patent No.: US 7,102,019 B2
(45) Date of Patent: Sep. 5, 2006

(54) COSMETIC AND PHARMACEUTICAL PREPARATIONS COMPRISING ASCORBIC ACID DERIVATIVES

(75) Inventors: Harald Streicher, Ludwigshafen (DE); Bernd Ostersehlt, Maxdorf (DE); Horst Westenfelder, Neustadt (DE)

(73) Assignee: BASF Aktiengesellschaft, Ludwigshafen (DE)

(*) Notice: Subject to any disclaimer, the term of this patent is extended or adjusted under 35 U.S.C. 154(b) by 697 days.

(21) Appl. No.: 09/967,530

(22) Filed: Oct. 1, 2001

(65) Prior Publication Data

US 2002/0034527 A1 Mar. 21, 2002

Related U.S. Application Data

(62) Division of application No. 09/186,385, filed on Nov. 5, 1998.

(30) Foreign Application Priority Data

Nov. 14, 1997 (DE) .......................... 197 50 526

(51) Int. Cl.
*C07D 307/62* (2006.01)

(52) U.S. Cl. ...................................... 549/315; 549/316
(58) Field of Classification Search ................. 549/315, 549/316
See application file for complete search history.

(56) References Cited

U.S. PATENT DOCUMENTS 2,980,702 A * 4/1961 Thesing et al. .......... 260/343.7

6,346,254 B1 * 2/2002 Streicher et al. ............ 424/401

OTHER PUBLICATIONS

Tanaka, H. et al '5,6–Isopropylideneascorbic Acid Derivatives' CA 73:99173 (1970).*

* cited by examiner

*Primary Examiner*—Amelia Owens
(74) *Attorney, Agent, or Firm*—Novak Druce DeLuca & Quigg, LLP; Jason D. Voight

(57) ABSTRACT

An ascorbic acid derivative of the formula Ia:

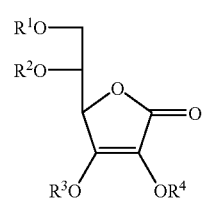

where the variables independently of one another have the following meanings:

$R^1$ and $R^2$ independently of one another are hydrogen or $C_1$–$C_{20}$-acyl;

$R^3$ is hydrogen or a cation selected from the group consisting of $NH_4^+$, alkali metal and alkaline earth metal cations;

$R^4$ is $C_1$–$C_6$-alkoxycarbonyl, and a process for its preparation.

4 Claims, No Drawings

COSMETIC AND PHARMACEUTICAL PREPARATIONS COMPRISING ASCORBIC ACID DERIVATIVES

This application is a divisional application of Ser. No. 09/186,385, filed Nov. 5, 1998.

Ascorbic acid (vitamin C) is an antioxidant which is widely employed in cosmetics. Together with vitamin E it counteracts the oxidation of unsaturated fatty acids and thus also prevents lipoperoxide formation (O. Isler, G. Brubacher, S. Ghisla, B. Kräutler eds.; Vitamine II (vitamins II), G. Thieme Verlag, Stuttgart, N. Y., 431, 1988). As a vitamin, ascorbic acid is also involved in the metabolism, for instance in the hydroxylation of proline in collagen synthesis (J. J. Burns, J. M. Rivers, L. J. Machin eds.; Third Conference on vitamin C, Ann. N. Y. Acad. Sci., 498 (1987) 1–533).

On account of the excessively low stability of ascorbic acid in cosmetic formulations, it is often necessary to employ stabilized derivatives of ascorbic acid. Examples of these are sodium L-ascorbate monophosphate (JP 07082127, JP 05331020), L-ascorbic acid 2-O-D-glucoside (T. Sakamoto et al.; 19th IFSCC Congress, Sydney, 1996, Vol. 2, Paper No. 14) and 5,6-isopropylidene-L-ascorbic acid 2-phosphate (JP 08269074).

The abovementioned stabilized ascorbic acid derivatives, however, frequently have the disadvantage that they are too poorly soluble in cosmetic or pharmaceutical oils.

It is therefore an object of the invention to make available stable ascorbic acid derivatives, which do not have the abovementioned disadvantages, for cosmetic and pharmaceutical preparations.

We have found that this object is achieved according to the invention by use of ascorbic acid derivatives of the formula I,

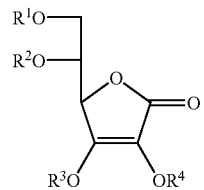

where the variables independently of one another have the following meanings:
  $R^1$ is hydrogen, $C_1$–$C_{20}$-acyl, $C_1$–$C_{12}$-alkoxycarbonyl, $C_1$–$C_{12}$-alkyl;
  $R^2$ is hydrogen, $C_1$–$C_{20}$-acyl, $C_1$–$C_{12}$-alkoxycarbonyl, $C_1$–$C_{12}$-alkyl,
  where $R^1$ and $R^2$, together with the oxygen atoms to which they are bonded and the carbon atoms bonded to the oxygen atoms, can form an unsubstituted or substituted heterocycle;
  $R^3$ is hydrogen or a cation selected from the group consisting of $NH_4^+$, alkali metal and alkaline earth metal cations;
  $R^4$ is $C_1$–$C_{12}$-alkoxycarbonyl,
  for cosmetic and pharmaceutical preparations.

Preferred compounds of formula I are those where the variables have the following meanings:
  $R^1$ is hydrogen, $C_1$–$C_{20}$-acyl, $C_1$–$C_{12}$-alkoxycarbonyl, $C_1$–$C_{12}$-alkyl;
  $R^2$ is hydrogen, $C_1$–$C_{20}$-acyl, $C_1$–$C_{12}$-alkoxycarbonyl, $C_1$–$C_{12}$-alkyl,
  where $R^1$ and $R^2$, together with the oxygen atoms to which they are bonded and the carbon atoms bonded to the oxygen atoms, can form an unsubstituted or substituted heterocycle and
  $R^1$ must not be a $C_1$–$C_{12}$-alkoxycarbonyl radical if $R^2$ is hydrogen;
  $R^3$ is hydrogen or a cation selected from the group consisting of $NH_4^+$, alkali metal and alkaline earth metal cations;
  $R^4$ is $C_1$–$C_{12}$-alkoxycarbonyl.

Very particularly preferred compounds of the formula I are those where the variables have the following meanings:
  $R^1$ is hydrogen, $C_1$–$C_{20}$-acyl, $C_1$–$C_6$-alkoxycarbonyl;
  $R^2$ is hydrogen, $C_1$–$C_{20}$-acyl, $C_1$–$C_6$-alkoxycarbonyl,
  where $R^1$ must not be a $C_1$–$C_6$-alkoxycarbonyl radical if $R^2$ is hydrogen;
  $R^3$ is hydrogen or a cation selected from the group consisting of $NH_4^+$, alkali metal and alkaline earth metal cations;
  $R^4$ is $C_1$–$C_6$-alkoxycarbonyl.

In the ascorbic acid derivatives of the formula I according to the invention, acyl radicals for $R^1$ and $R^2$ are to be understood as meaning branched or unbranched, saturated or unsaturated, if appropriate polyunsaturated, $C_1$–$C_{20}$-acyl chains.

Examples of these are acyl radicals of formic, acetic, propionic, n-butyric, isobutyric, sorbic, n-valeric, isovaleric, caproic, caprylic, capric, undecanoic, lauric, tridecanoic, myristic, pentadecanoic, palmitic, palmitoleic, stearic, oleic, linoleic, linolenic, nonadecanoic and arachidonic acid.

Preferred acyl radicals are those of long-chain fatty acids having $C_{10}$ to $C_{20}$ carbon chains, in particular acyl radicals of lauric, palmitic, palmitoleic, stearic, oleic and linoleic acid.

Alkyl radicals $R^1$ and $R^2$ which may be mentioned are branched or unbranched $C_1$–$C_{12}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl.

Particularly preferred alkyl radicals are $C_1$–$C_6$-alkyl chains, in particular methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl.

The radicals $R^1$ and $R^2$, together with the oxygen atoms to which they are bonded and the carbon atoms bonded to the oxygen atoms, can form unsubstituted or substituted heterocycles. These are intended to include, for example, cyclic acetals and ketals which, inter alia, are employed as a protective group for the two terminal hydroxyl functions (in the 5- and 6-position) of the acorbic acid. A preferred heterocyclic system is, inter alia, the 5,6-isopropylidene radical, which is formed by reaction of the two free hydroxyl groups in the 5- and 6-position with acetone.

Suitable alkoxycarbonyl radicals for $R^1$, $R^2$ and $R^4$ are those whose alkoxy group contains 1 to 12 C atoms, preferably 1 to 6 C atoms, particularly preferably 1 to 4 C atoms.

Examples of the preferred radicals which may be mentioned are:

methoxycarbonyl ethoxycarbonyl
isopropoxycarbonyl n-propoxycarbonyl
1-methylpropoxycarbonyl n-butoxycarbonyl
n-pentoxycarbonyl 2-methylpropoxycarbonyl
3-methylbutoxycarbonyl 1,1-dimethylpropoxycarbonyl
2,2-dimethylpropoxycarbonyl hexoxycarbonyl
1-methyl-1-ethylpropoxycarbonyl Particularly preferred alkoxycarbonyl radicals are:

methoxycarbonyl ethoxycarbonyl
sopropoxycarbonyl n-propoxycarbonyl
1-methylpropoxycarbonyl n-butoxycarbonyl Possible cations for $R^3$ are $NH_4^+$ and representatives from the group consisting of the alkali and alkaline earth metals, preferably Na, K, Li, Ca and Mg, particularly preferably Na, K and Mg.

The term ascorbic acid derivatives is understood as meaning both derivatives of L- and D-ascorbic acid (isoascorbic acid), preferably L-ascorbic acid.

Some di- and tricarbonates of ascorbic acid are already known. Thus U.S. Pat. No. 2,980,702 describes compounds of the 2,5,6-tri-O-($C_1$–$C_3$-alkoxycarbonyl)-L-ascorbic acid type and their use as a heat-resistant additive in foodstuffs, especially in baked goods. JP 42020050 describes the synthesis of 2,6-di-O-($C_1$–$C_3$-alkoxycarbonyl)-L-ascorbic acid as a heat-stable derivative of ascorbic acid.

The use of the abovementioned ascorbic acid derivatives in cosmetic and pharmaceutical applications, however, is novel.

The stable ascorbic acid derivatives of the formula I according to the invention are outstandingly suitable as active compounds for cosmetic and pharmaceutical preparations.

Thus the compounds are distinguished, inter alia, in that, by variation of the radicals $R^1$, $R^2$ and $R^4$, the lipophilicity of the ascorbic acid derivatives can be adjusted in a controlled manner. Depending on the demand in the formulation of cosmetic and pharmaceutical preparations, a wide range of stable vitamin C derivatives is thus available to the expert in the field. The tricabonates and the fatty acid esters of vitamin C 2-mono-carbonate particularly can be incorporated very readily into preparations such as, for example, ointments, lotions, gels or emulsions on account of their good oil solubility.

Accordingly, the present invention also relates to cosmetic and pharmaceutical preparations comprising an effective amount of at least one of the compounds of the formula I, and customary cosmetic and pharmaceutical auxiliaries and additives.

The abovementioned preparations can contain the compounds of the formula I in proportions of from 0.01 to 10% by weight, preferably 0.1 to 8% by weight, particularly preferably 0.5 to 5% by weight, based on the total amount of the cosmetic or pharmaceutical preparation.

The ascorbic acid derivatives of the formula I can be employed, inter alia, in all cosmetic and pharmaceutical preparations which, in addition to water, also contain emulsifiers, stabilizers, natural oils, cosmetic oils, fats, waxes, silicone oils, silicone oil derivatives, solubilizers, sunscreens, moisturizers, active compounds, consistency-imparting agents, gel-forming agents, antioxidants or preservatives.

Emulsifiers used are, for example, the following substances:

Polyglycerol fatty acid esters, ethoxylates of fatty acids, sorbitan fatty acid esters, phosphoric acid esters of fatty acids, phospholipids, glycerol monostearate and self-emulsifying glycerol monostearate.

Stabilizers are understood as meaning:

Magnesium and aluminum salts of fatty acids, complexing agents such as EDTA, NTA, MGDA, antioxidants such as BHT, BHA, alpha tocopherol, gallic acid and its salts and esters.

Natural oils are, for example, jojoba oil, sunflower oil, groundnut oil, almond oil, avocado oil, macadamia nut oil, castor oil, maize germ oil, grapeseed oil.

Cosmetic oils are, for example, isopropyl esters of fatty acids, very particularly isopropyl stearate, isopropyl palmitate, isopropyl isostearate, isopropyl myristate, isopropyl laurate, paraffin oil, neutral oil.

Cosmetic active compounds are, for example, panthenol, bisabolol, α-tocopherol, α-tocopheryl acetate, Aloe vera, algal extract, hyaluronic acid, retinol and retinyl esters, phytantriol, panthenyl ethyl ether, ferulic acid.

Sunscreens which can be used on their own or as a mixture together with the compounds of the formula I are, for example

| No. | Substance | CAS No. (= acid) |
|---|---|---|
| 1 | 4-Aminobenzoic acid | 150-13-0 |
| 2 | 3-(4'-Trimethylammonium)benzylidene-bornan-2-one methylsulfate | 52793-97-2 |
| 3 | 3,3,5-Trimethylcyclohexyl salicylate (homosalate) | 118-56-9 |
| 4 | 2-Hydroxy-4-methoxy-benzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methane-sulfonic acid) and its salts | 90457-82-2 |
| 7 | Polyethoxyethyl 4-bis (polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzane) and the sodium salt | 4065-45-6 |
| 13 | 3-(4'-Methyl)benzylidenebornan-2-one | 36861-47-9 |
| 14 | 3-Benzylidenebornan-2-one | 15087-24-8 |
| 15 | 1-(4'-Isopropylphenyl)-3-phenylpropane-1,3-dione | 63250-25-9 |
| 16 | 4-Isopropylbenzyl salicylate | 94134-93-7 |
| 17 | 2,4,6-Trianiline-(o-carbo-2'-ethyl-hexyl-1'-oxy)-1,3,5-triazine | 88122-99-0 |
| 18 | 3-Imidazol-4-ylacrylic acid and its ethyl ester | 104-98-3 |
| 19 | Ethyl 2-cyano-3,3-diphenylacrylate | 5232-99-5 |
| 20 | 2'-Ethylhexyl 2-cyano-3,3-diphenylacrylate | 6197-30-4 |
| 21 | Methyl o-aminobenzoate or: 5-methyl-2-(1-methylethyl)-2-aminobenzoate | 134-09-8 |
| 22 | Glyceryl p-aminobenzoate or: 1-glyceryl 4-aminobenzoate | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexenone) | 1641-17-4 |
| 25 | Triethanolamine salicylate | 2174-16-5 |
| 26 | Dimethoxyphenylglyoxalic acid or: sodium 3,4-dimethoxyphenylglyoxalate | 4732-70-01 |
| 27 | 3-(4'-Sulfo)benzylidenebornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |

The ascorbic acid derivatives of the formula I are also suitable for surfactant formulations.

Thus hair rinses, shampoos, and foams with stable vitamin C of the formula I can be prepared without problems.

The combination of anionic and cationic surfactants does not restrict use in cosmetic products.

The invention furthermore relates to ascorbic acid derivatives of the formula Ia,

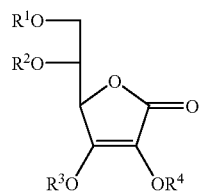

Ia where the variables independently of one another have the following meanings:
  $R^1$ and $R^2$ independently of one another are hydrogen or $C_1$–$C_{20}$-acyl;
  $R^3$ is hydrogen or a cation selected from the group consisting of alkali metals and alkaline earth metals;
  $R^4$ is $C_1$–$C_6$-alkoxycarbonyl.

Also claimed are ascorbic acid derivatives of the formula Ib,

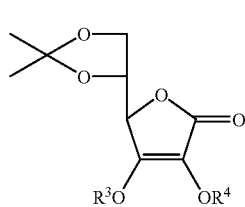

Ib where
  $R^3$ is hydrogen or a cation selected from the group consisting of alkali metals and alkaline earth metals, and
  $R^4$ is $C_1$–$C_6$-alkoxycarbonyl.

Acyl radicals for $R^1$ and $R^2$ are understood as meaning branched or unbranched, saturated or unsaturated, if appropriate polyunsaturated, $C_1$–$C_{20}$-acyl chains.

Examples of these are acyl radicals of the formic, acetic, propionic, n-butyric, isobutyric, n-valeric, isovaleric, caproic, caprylic, capric, undecanoic, lauric, tridecanoic, myristic, pentadecanoic, palmitic, palmitoleic, stearic, oleic, linoleic, linolenic, nonadecanoic and arachidonic acid.

Preferred acyl radicals are those of long-chain fatty acids having $C_{10}$ to $C_{20}$ carbon chains, in particular acyl radicals of lauric, palmitic, palmitoleic, stearic, oleic and linoleic acid.

Suitable alkoxycarbonyl radicals for $R^4$ are those whose alkoxy group contains from 1 to 6 C atoms, particularly preferably 1 to 4 C atoms.

Particularly preferred alkoxycarbonyl radicals are:
  methoxycarbonyl ethoxycarbonyl
  isopropoxycarbonyl n-propoxycarbonyl
  1-methylpropoxycarbonyl n-butoxycarbonyl Possible cations for $R^3$ are representatives of the group consisting of the alkali metals and alkaline earth metals, preferably Na, K, Li, Ca and Mg, particularly preferably Na, K and Mg.

The synthesis of the ascorbic acid derivatives of the formulae Ia and Ib, starting from the starting materials IIa and IIb, is carried out analogously to the process according to Japanese Patent Publication JP 42020050. Reference is made to this publication with respect to closer details.

In the following examples, the preparation of the ascorbic acid derivatives of the formula I according to the invention and the composition of cosmetic formulations which contain these ascorbic acid derivatives is illustrated in greater detail.

EXAMPLE 1

2,5,6-Tri-O-(isopropyloxycarbonyl)-L-ascorbic acid 1.5 l (1.5 mol) of a 1 M solution of isopropyl chloroformate in toluene were added dropwise at −15° C. to 80 g (0.454 mol) of L-ascorbic acid in 350 ml (4.3 mol) of pyridine, pyridinium hydrochloride being deposited as a white precipitate. The resulting suspension was stirred at room temperature for a further 1.5 hours and the pyridinium hydrochloride was then filtered off. The yellow filtrate was concentrated in vacuo and the reddish, oily crude product arising therefrom was washed twice with 1 M HCl solution after taking up in dichloromethane. The organic lower phase was then extracted four times with saturated (10% strength) sodium hydrogencarbonate solution and the combined aqueous extracts (in each case upper phases) were treated with conc. hydrochloric acid up to the commencement of turbidity (about pH 1). This aqueous suspension was then extracted three times with dichloromethane and the combined organic extracts (in each case lower phases) were dried over $Na_2SO_4$ and concentrated in vacuo. After vacuum drying, a yellow wax was obtained.

Yield: 68.0 g (34.5%)

$^{13}$C-NMR: δ=165.82 (CO-ascorbyl), 154.90 (C-3-ascorbyl), 154.06, 153.58, 153.09 (3× CO-carbonate), 115.04 (C-2-ascorbyl), 76.02 (C-4-ascorbyl), 73.63, 73.25, 73.13 (3× $CH(CH_3)_2$), 72.88 (C-5-ascorbyl), 64.44 (C-6-ascorbyl), 21.70, 21.69, 21.56, 21.54, 21.48, 21.47 (6× $CH_3$) ppm.

EXAMPLE 2

6-O-Palmitoyl-2-O-(isopropyloxycarbonyl)-L-ascorbic acid 45 ml (0.045 mol) of a 1 M solution of isopropyl chloroformate in toluene were added dropwise at −15° C. to 17.8 g (0.042 mol) of 6-O-palmitoyl-L-ascorbic acid in 100 ml (1.24 mol) of pyridine. The reaction mixture was stirred at room temperature for a further hour and the deposited pyridinium hydrochloride was filtered off. The yellow filtrate was concentrated in vacuo with repeated codistillation with toluene.

The brown oily residue was taken up in dichloromethane/toluene (1:1) and washed twice with 1 M HCl solution. Drying of the organic phase over $Na_2SO_4$ and concentration in vacuo yielded a dark yellow to brown solid, which, in divided form after suspending twice in a little cold ethyl acetate, was filtered as a white solid.

Final weight: 13.3 g (61.9%)

$^{13}$C-NMR: δ=174.11 (CO-palmitoyl), 166.80 (CO-ascorbyl), 156.62 (OCOO-carbonate), 153.23 (C-3-ascorbyl), 114.60 (C-2-ascorbyl), 75.98 (C-4-ascorbyl); 75.60 ($OCH(CH_3)_2$); 67.94 (C-5-ascorbyl); 64.43 (C-6-ascorbyl); 34.10 (C-2-palmitoyl) ppm.

EXAMPLE 3

5,6-O-Isopropylidene-2-O-(isopropyloxycarbonyl)-L-ascorbic acid 415 ml (0.415 mol) of a 1 M solution of isopropyl chloroformate in toluene were added dropwise at −15° C. to 85.3 g (0.395 mol) of 5,6-O-isopropylidene-L-ascorbic acid in 300 ml (3.7 mol) of pyridine, pyridinium hydrochloride being deposited as a white solid. The mixture was stirred at room temperature for a further hour and the pyridinium hydrochloride was then filtered off. The yellow filtrate was concentrated in vacuo with repeated codistillation with toluene. The orange syrup thus obtained was taken up in dichloromethane/toluene (1:1), washed twice with 1 M HCl solution and extracted four times in each case with saturated (10% strength) sodium hydrogencarbonate solution. The combined aqueous upper phases were treated with conc. hydrochloric acid until the solution became turbid. The aqueous suspension thus formed was extracted three times with dichloromethane with taking up of the deposited solid. The combined organic extracts were dried over $Na_2SO_4$ and concentrated in vacuo to obtain a yellow solid.

Yield: 86 g (72.1%).

Recrystallization of this colored crude solid from a little warm dichloromethane and suspension of the crystallizate in a little cold ethyl acetate with subsequent filtration yielded a white crystallizate.

Yield after recrystallization: 47.2 g (39.5%)

$^{13}$C-NMR: δ=166.21 (CO-ascorbyl), 155.13 (CO-carbonate), 153.46 (C-2-ascorbyl), 114.79 (C-3-ascorbyl), 110.71 ($C(CH_3)_2$), 76.03 (C-4-ascorbyl), 74.74 ($CH(CH_3)_2$), 73.52 (C-5-ascorbyl), 65.28 (C-6-ascorbyl), 25.78, 25.55 ($C(CH_3)_2$), 21.51, 21.50 ($CH(CH_3)_2$) ppm.

EXAMPLE 4

2-O-(Isopropyloxycarbonyl)-L-ascorbic acid 47 g (0.155 mol) of 5,6-O-isopropylidene-2-O-(isopropyl-oxycarbonyl)-L-ascorbic acid were stirred for 12 hours at room temperature in 200 ml of a trifluoroacetic acid/water mixture (1:4). The colorless reaction solution was concentrated in vacuo with repeated codistillation. A pale brown syrup (56.4 g, 138.3%) was obtained, which was purified on silica gel (eluent: dichloromethane/methanol 3:1).

Yield: 43 g (92%)

$^1$H-NMR: δ=4.81 (H-4), 4.77 ($OCH(CH_3)_2$), 3.77 (H-5), 3.49 (2× H-6), 1.30–1.25 ($OCH(CH_3)_2$) ppm.

Cosmetic preparations

EXAMPLE 5
Composition for Fat-free Sunscreen Gel

| Mass content (% by weight) | |
|---|---|
| 0.40 | Acrylate/$C_{10}$–$C_{30}$ alkylacrylate crosspolymer |
| 0.25 | Hydroxyethylcellulose |
| 8.00 | Octyl methoxycinnamate |
| 1.00 | 4-Methylbenzylidenecamphor |
| 0.50 | 6-O-Palmitoyl-2-O-(isopropyloxycarbonyl)-L-ascorbic acid |
| 0.20 | Disodium EDTA |
| 5.00 | Glycerol |
| 0.15 | Fragrance |
| 0.30 | Imidazolidinyl urea |
| 0.25 | Sodium methylparaben |
| 0.15 | Sodium propylparaben |
| 5.00 | PEG-25 PABA |
| 0.10 | Sodium hydroxide |
| to 100 | Water |

EXAMPLE 6
Composition for Moisturizing Cream

| Mass content (% by weight) | |
|---|---|
| 6.00 | PEG-7-hydrogenated castor oil |
| 5.00 | Isopropyl palmitate |
| 6.00 | Mineral oil |
| 5.00 | Jojoba oil |
| 5.00 | Almond oil |
| 0.50 | Tocopheryl acetate |
| 2.00 | 6-O-Palmitoyl-2-O-(isopropyloxycarbonyl)-L-ascorbic acid |
| 0.60 | Magnesium stearate |
| 2.00 | PEG-45/dodecyl glycol copolymer |
| 5.00 | Glycerol |
| 0.25 | Methylparaben |
| 0.15 | Propylparaben |
| 5.00 | Imidazolidinylurea |
| 0.15 | Fragrance |
| 0.20 | Disodium EDTA |
| to 100 | Water |

EXAMPLE 7
Composition for Moisturizing Cream

| Mass content (% by weight) | |
|---|---|
| 6.00 | PEG-7-hydrogenated castor oil |
| 5.00 | Isopropyl palmitate |
| 6.00 | Mineral oil |
| 5.00 | Jojoba oil |
| 5.00 | Almond oil |
| 0.50 | Tocopheryl acetate |
| 2.00 | 5,6-O-Isopropylidene-2-O-(isopropyloxycarbonyl)-L-ascorbic acid |
| 0.60 | Magnesium stearate |
| 2.00 | PEG-45/dodecyl glycol copolymer |
| 5.00 | Glycerol |
| 0.25 | Methylparaben |
| 0.15 | Propylparaben |
| 5.00 | Imidazolidinylurea |
| 0.15 | Fragrance |
| 0.20 | Disodium EDTA |
| to 100 | Water |

EXAMPLE 8
Composition for Night Cream without Preservative

| Mass content (% by weight) | |
|---|---|
| 5.00 | PEG-7-hydrogenated castor oil |
| 4.00 | Isopropyl palmitate |
| 4.00 | Caprylic acid/caprate triglyceride |
| 3.00 | 6-O-Palmitoyl-2-O-(isopropyloxycarbonyl)-L-ascorbic acid |
| 1.50 | PEG-45/dodecyl glycol copolymer |
| 0.50 | Magnesium stearate |
| 1.50 | Dimethicone |
| 4.00 | 1,2-Propylene glycol |
| 4.00 | Glycerol |
| 8.00 | 611 alcohol |
| 2.00 | Collagen |
| 0.15 | Fragrance |
| to 100 | Water |

EXAMPLE 9
Composition for Antiwrinkle Cream

| Mass content (% by weight) | |
|---|---|
| 6.00 | PEG-7-hydrogenated castor oil |
| 5.00 | Isopropyl palmitate |
| 10.00 | Mineral oil |
| 3.00 | Caprylic acid/caprate triglyceride |
| 0.60 | Magnesium stearate |
| 1.00 | 6-O-Palmitoyl-2-O-(isopropyloxycarbonyl)-L-ascorbic acid |
| 1.50 | Tocopheryl acetate |
| 2.00 | PEG-45/dodecyl glycol copolymer |
| 0.05 | Tocopherol |
| 0.20 | Retinol |
| 0.30 | Glycerol |
| 0.70 | Magnesium sulfate |
| 0.25 | Methylparaben |
| 0.15 | Propylparaben |
| 0.20 | Sodium ascorbyl monophosphate |
| 0.10 | α-Tocopherol |
| 0.10 | Ascorbyl palmitate |
| 0.15 | Fragrance |
| to 100 | Water |

EXAMPLE 10
Composition for Antiwrinkle Cream

| Mass content (% by weight) | |
|---|---|
| 6.00 | PEG-7-hydrogenated castor oil |
| 5.00 | Isopropyl palmitate |
| 10.00 | Mineral oil |
| 3.00 | Caprylic acid/caprate triglyceride |
| 0.60 | Magnesium stearate |
| 1.00 | 2,5,6-Tri-O-(isopropyloxycarbonyl)-L-ascorbic acid |
| 1.50 | Tocopheryl acetate |
| 2.00 | PEG-45/dodecyl glycol copolymer |
| 0.05 | Tocopherol |
| 0.20 | Retinol |
| 0.30 | Glycerol |
| 0.70 | Magnesium sulfate |
| 0.25 | Methylparaben |
| 0.15 | Propylparaben |
| 0.20 | Sodium ascorbyl monophosphate |
| 0.10 | α-Tocopherol |
| 0.10 | Ascorbyl palmitate |
| 0.15 | Fragrance |
| to 100 | Water |

EXAMPLE 11
Composition for Moisturizing Day Cream

| Mass content (% by weight) | |
|---|---|
| 2.00 | Ceteareth/6 |
| 2.00 | Ceteareth/25 |
| 10.00 | Mineral oil |
| 3.00 | Caprylic acid/caprate triglyceride |
| 3.00 | Isostearic acid |
| 3.00 | 6-O-Palmitoyl-2-O-(isopropyloxycarbonyl)-L-ascorbic acid |
| 1.50 | Tocopheryl acetate |
| 2.00 | D-Panthenol USP |
| 0.05 | Tocopherol |
| 0.20 | Retinol |
| 0.30 | Glycerol |
| 0.13 | Dibromocyanobutane |
| 0.20 | Sodium ascorbyl monophosphate |
| 0.10 | α-Tocopherol |
| 0.10 | Ascorbyl palmitate |
| 0.15 | Fragrance |
| to 100 | Water |

EXAMPLE 12
Composition for Moisturizing Day Cream

| Mass content (% by weight) | |
|---|---|
| 2.00 | Ceteareth/6 |
| 2.00 | Ceteareth/25 |
| 10.00 | Mineral oil |
| 3.00 | Caprylic acid/caprate triglyceride |
| 3.00 | Isostearic acid |
| 3.00 | 2-O-(isopropyloxycarbonyl)-L-ascorbic acid |
| 1.50 | Tocopheryl acetate |
| 2.00 | D-Panthenol USP |
| 0.05 | Tocopherol |
| 0.20 | Retinol |
| 0.30 | Glycerol |
| 0.15 | Dibromocyanobutane |
| 0.20 | Sodium ascorbyl monophosphate |
| 0.10 | α-Tocopherol |
| 0.10 | Ascorbyl palmitate |
| 0.15 | Fragrance |
| to 100 | Water |

We claim:

1. An ascorbic acid derivative of the formula Ia:

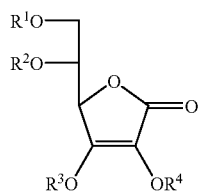

where the variables independently of one another have the following meanings:

$R^1$ and $R^2$ independently of one another are hydrogen or $C_1$–$C_{20}$-acyl;

$R^3$ is hydrogen or a cation selected from the group consisting of $NH_4^+$, alkali metal and alkaline earth metal cations;

$R^4$ is $C_1$–$C_6$-alkoxycarbonyl.

2. A process for preparing ascorbic acid derivatives of the formula Ia, which comprises reacting an ascorbic acid derivative of the formula IIa:

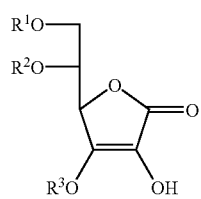

IIa where the substituents $R^1$ to $R^3$ have the meanings mentioned in claim 1, with an alkyl halocarbonate of chain length $C_1$ to $C_6$.

3. A process for preparing ascorbic acid derivatives of the formula Ib, which comprises reacting an ascorbic acid derivative of the formula IIb:

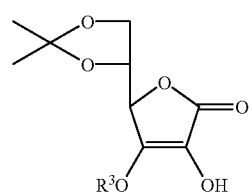

IIb where $R^3$ has the meaning mentioned in claim 1, with an alkyl halocarbonate of chain length $C_1$ to $C_6$.

4. A process for preparing ascorbic acid derivatives as claimed in claim 2, which comprises using alkyl chloro- or bromocarbonates of chain length $C_1$ to $C_6$.

* * * * *